USO11123088B2

(12) United States Patent
Tyndall et al.

(10) Patent No.: US 11,123,088 B2
(45) Date of Patent: Sep. 21, 2021

(54) PRESSURE ACTIVATED SURGICAL TOOL FOR USE IN SPINAL DECOMPRESSION PROCEDURES AND METHODS OF USING THE SAME

(71) Applicant: Spinal Innovations, LLC, Dyer, IN (US)

(72) Inventors: Dwight S. Tyndall, Chicago, IL (US); Kevin Chappuis, Malden, MA (US); Nicholas Uvanovic, Norfolk, MA (US)

(73) Assignee: SPINAL INNOVATIONS, LLC, Dyer, IN (US)

( * ) Notice: Subject to any disclaimer, the term of this patent is extended or adjusted under 35 U.S.C. 154(b) by 0 days.

(21) Appl. No.: 17/149,945

(22) Filed: Jan. 15, 2021

(65) Prior Publication Data

US 2021/0219997 A1 Jul. 22, 2021

Related U.S. Application Data

(60) Provisional application No. 62/961,811, filed on Jan. 16, 2020.

(51) Int. Cl.
| | |
|---|---|
| *A61B 17/17* | (2006.01) |
| *A61B 90/00* | (2016.01) |
| *A61B 17/16* | (2006.01) |
| *A61B 34/20* | (2016.01) |

(Continued)

(52) U.S. Cl.
CPC ...... *A61B 17/1757* (2013.01); *A61B 17/1615* (2013.01); *A61B 17/1626* (2013.01); *A61B 17/1631* (2013.01); *A61B 34/10* (2016.02); *A61B 34/20* (2016.02); *A61B 34/30* (2016.02); (Continued)

(58) Field of Classification Search
CPC ................. A61B 17/1757; A61B 2090/031
See application file for complete search history.

(56) References Cited

U.S. PATENT DOCUMENTS

| | | |
|---|---|---|
| 2,842,131 A | 7/1958 | Smith |
| 4,310,269 A | 1/1982 | Neu et al. |
| 4,456,010 A | 6/1984 | Reimels et al. |

(Continued)

FOREIGN PATENT DOCUMENTS

| | | |
|---|---|---|
| CN | 102485177 A | 6/2012 |
| CN | 203693685 U | 7/2014 |

(Continued)

*Primary Examiner* — Christian A Sevilla
(74) *Attorney, Agent, or Firm* — Thompson Hine LLP

(57) ABSTRACT

A surgical tool for use in a system for removing bone from vertebrae to relieve stenosis is provided. In one embodiment, the surgical tool includes a drill bit having a proximal end and a distal end, a drive shaft having a proximal rod portion and a distal tubular portion, the drill bit and the drive shaft configured to rotate about a horizontal axis in a clockwise direction; and an engagement system disposed between the drill bit and the drive shaft; wherein the engagement system is configured to selectively engage the drill bit to the drive shaft for powered rotation when the drill bit contacts a first material at a first predetermined resistance and to disengage the drill bit from the drive shaft when the drill bit engages a second material at a second predetermined resistance; and wherein the first predetermined resistance is greater than the second predetermined resistance.

17 Claims, 21 Drawing Sheets

(51) Int. Cl.
  *A61B 34/30* (2016.01)
  *A61B 34/10* (2016.01)
(52) U.S. Cl.
  CPC ........ *A61B 90/06* (2016.02); *A61B 2034/107* (2016.02); *A61B 2090/064* (2016.02)

(56) References Cited

U.S. PATENT DOCUMENTS

| | | |
|---|---|---|
| 4,600,006 A | 7/1986 | Baker |
| 4,830,001 A | 5/1989 | Walus |
| 5,330,480 A | 7/1994 | Meloul et al. |
| 6,336,931 B1 | 1/2002 | Hsu et al. |
| 9,283,048 B2 | 3/2016 | Kostrzewski et al. |
| 9,561,544 B2 | 2/2017 | Walsh et al. |
| 10,292,778 B2 | 5/2019 | Kostrzewski et al. |
| 10,517,681 B2 | 12/2019 | Roh et al. |
| 10,531,927 B2 | 1/2020 | Crawford et al. |
| 2007/0260257 A1* | 11/2007 | Phan ................ B25B 23/1427 606/84 |
| 2008/0195081 A1 | 8/2008 | Moll |
| 2009/0024129 A1 | 1/2009 | Gordon et al. |
| 2009/0293687 A1* | 12/2009 | Nino ....................... B25B 15/02 81/476 |
| 2011/0243673 A1 | 10/2011 | Svagr |
| 2013/0152746 A1* | 6/2013 | Kerboul ................ B25B 13/466 81/475 |
| 2014/0371751 A1 | 12/2014 | Thomas |
| 2017/0056116 A1 | 3/2017 | Kostrzewski |
| 2018/0263714 A1 | 9/2018 | Kostrzewski et al. |

FOREIGN PATENT DOCUMENTS

| | | | |
|---|---|---|---|
| FR | 2492655 A1 | 4/1982 | |
| JP | 2017536909 | 12/2017 | |
| JP | 2018158104 A | 10/2018 | |
| KR | 20090117477 A | 11/2009 | |
| WO | 2009/136775 A2 | 11/2009 | |
| WO | WO-2013143563 A1 * | 10/2013 | ......... A61B 17/1622 |
| WO | WO-2017062290 A1 * | 4/2017 | ........... B25B 23/141 |
| WO | 2018/165390 A1 | 9/2018 | |

* cited by examiner

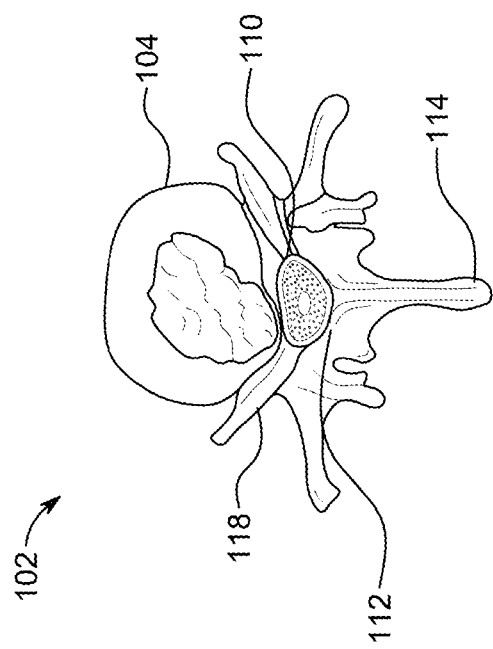
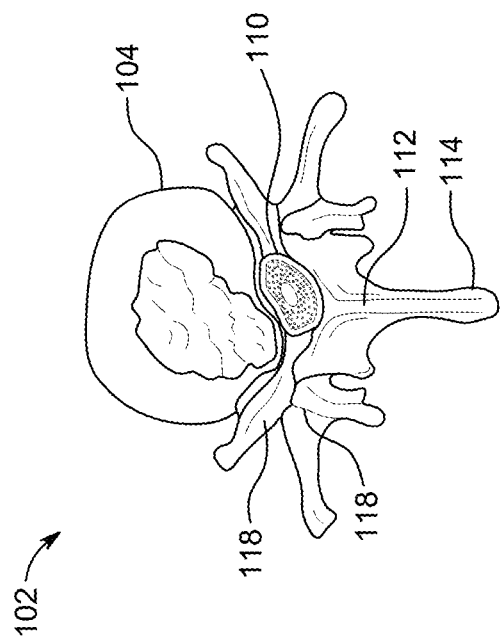
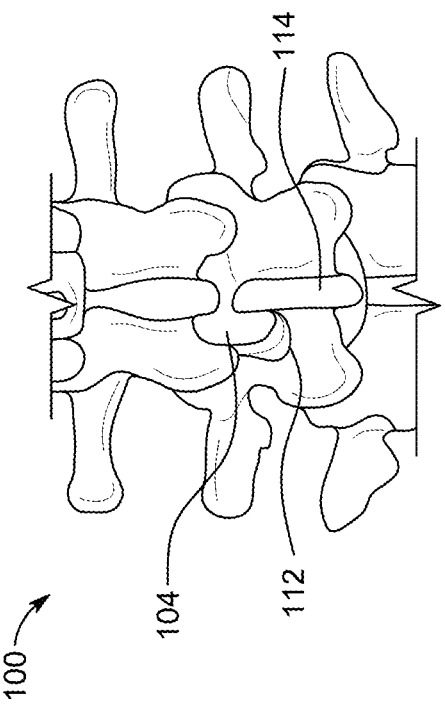
FIG. 6A
FIG. 6B
FIG. 6C

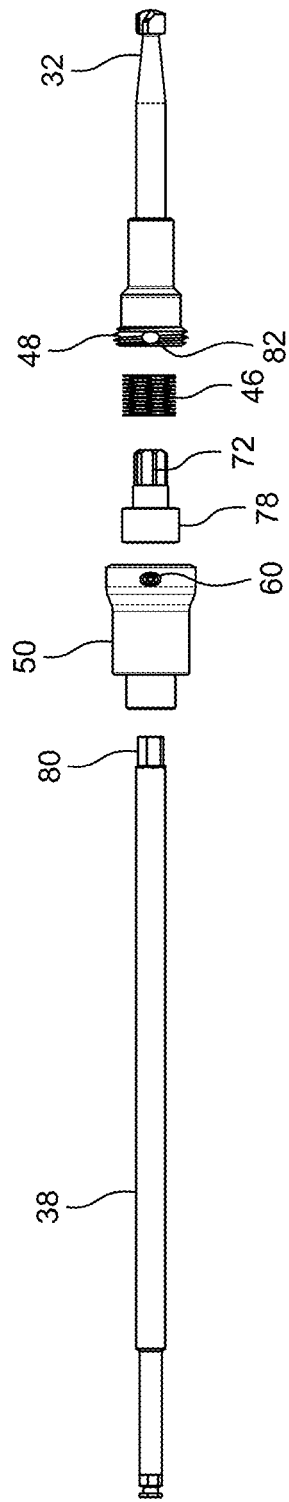
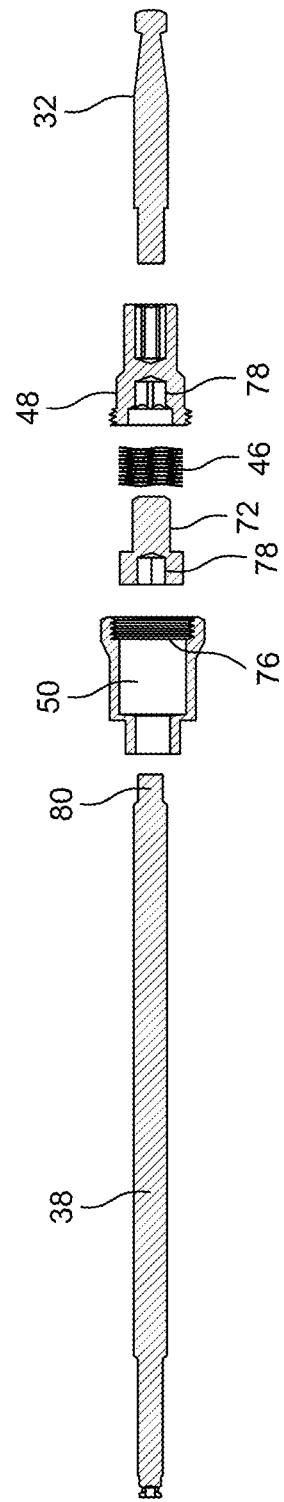
FIG. 20
FIG. 21

PRESSURE ACTIVATED SURGICAL TOOL FOR USE IN SPINAL DECOMPRESSION PROCEDURES AND METHODS OF USING THE SAME

RELATED APPLICATIONS

This application claims priority to U.S. Prov. Appln. No. 62/961,811, filed Jan. 16, 2020, entitled "Robot-Guided Spinal Decompression" which is incorporated herein by reference.

FIELD OF THE INVENTION

The disclosure generally relates to spinal surgery. Stated more particularly, disclosed herein are systems and methods for the decompression of spinal stenosis through laminotomy or laminectomy techniques performed under robotic guidance.

BACKGROUND OF THE INVENTION

The human spine is a complex structure with thirty-three individual vertebrae stacked atop one another. The spinal column provides the main support for the torso of the human body allowing flexible, multi-directional movement, while protecting the spinal cord from injury. As shown in FIGS. 2 through 5, a human spine 100 is depicted with plural vertebrae 102, each with an anterior vertebral body 104 and a posterior vertebral arch 106 that cooperate to enclose the vertebral foramen 108 through which the spinal cord 110 passes. The vertebral arch 106 includes a pair of laminae 112 and a spinous process 114 there between. The vertebrae 102 are joined by facet joints 116. Spinal nerves 118 leave the spinal cord 110 through intervertebral foramina 120. Anterior (not shown) and posterior longitudinal ligaments 122 extend the length of the vertebral column, and dura mater 124 envelops the spinal cord 110.

The narrowing of one or more of the foramina 108 or 120 within the spine 100 is generally referred to as spinal stenosis. That narrowing of the foramina 108 or 120 reduces the space available for the comfortable and effective passage of nerves 118. Spinal stenosis can come to exist within the vertebral foramen (collectively, the spinal canal) 108 or within the intervertebral foramina 120 where spinal nerves 118 exit the spinal canal 108.

Depending on the location and the severity of the narrowing, compression of the spinal nerve 118 or the spinal cord 110 can produce symptoms that can range in severity and that can include pain, tingling, numbness, and weakness. Pain deriving from spinal stenosis can be sharp and can radiate into one or more of the person's arms or legs, or it may be dull and localized to the neck or lower back. Where numbness occurs, it may vary from reduced sensitivity to total numbness in an arm, leg, or other portion of the body. Spinal stenosis can also lead to strength deterioration, loss of coordination, and still further deleterious consequences.

Certain instances of spinal stenosis can be treated non-surgically, such as with physical therapy, pain medication, activity modification, or epidural injection. Where non-surgical treatment is insufficient to alleviate the effects of spinal stenosis, surgical intervention may become necessary.

According to one known method of treatment, an invasive fusion procedure is performed where adjacent vertebrae 102 are fused together with screws and rods to stabilize the spine, normally after a spinal decompression technique has been performed. Such fusion procedures introduce increased surgical risk and are known to carry the risk of unintended negative long-term consequences.

An alternative treatment is a laminotomy procedure where at least a portion of the laminae 112 and/or the spinous process 114, the bony protrusion at the back of the vertebra 102 that connects them, is removed, as depicted in FIGS. 6A, B, and C. This removal of part of the vertebral arch 106 is designed to decompress the spinal cord 110 and nerve roots 118 that were being pinched or inflamed by spinal stenosis. When done successfully, laminotomy surgery can eliminate the need for a more invasive fusion procedure. However, the laminotomy can be technically challenging. It requires extreme precision to remove just enough lamina 112 or spinous process 114 bone to decompress the spine 100 without compromising the remaining lamina 112, spinous process 114, facet joints 116, or stabilizing ligaments 122.

As shown in FIGS. 7A and B, another available surgical treatment is a laminectomy where the entire lamina 112 and spinous process 114 are removed. A laminectomy introduces further risk of destabilization as the posterior stabilizing portion of the spine 100 is removed. It is recognized to be an inherently ablative and often imprecise procedure, one performed on the lamina bone 112 as it resides directly over the spinal cord 110. Injury to the spinal cord 110 can carry extreme immediate and long-term consequences to the patient.

It is normally up to the surgeon's skill and accuracy to cut to the required depth successfully without injuring surrounding nerves 118 or unduly compromising the stabilizing anatomy, such as the facet joint 116 or interspinous ligaments 122. Deficits in physician skill or accuracy can lead to devastating consequences or ineffective procedures.

In other surgical techniques, it is known to use robotic control, such as to drill precise pilot holes for bone screws in fusion procedures. The use of such robotic systems seeks to provide improved accuracy and effectiveness of the surgery. However, the application of robotic guidance has been limited in the field.

One major obstacle to the use of robotic control in laminotomy and laminectomy procedures is the critical need for human differentiation between the drilling and removal of bone as compared to drilling into the softer tissue of ligaments, joints, and nerves. Also preventing robotic control is need for determining and accurately acting in relation to the location of the needed material removal.

It has been appreciated that a robotic surgical solution capable of autonomous or semi-autonomous operation in performing laminotomy and laminectomy procedures would represent a substantial advance in the art. It has been further appreciated that the practical application of such robot-guided procedures demands concomitant advances in mechanical and operational characteristics, including the effective differentiation between bone and tissue.

SUMMARY OF THE INVENTION

In one embodiment, a surgical tool for use in a system for removing bone from vertebrae to relieve stenosis includes: a drill bit having a proximal end and a distal end, a drive shaft having a proximal rod portion and a distal tubular portion, the drill bit and the drive shaft configured to rotate about a horizontal axis in a clockwise direction; and an engagement system disposed between the drill bit and the drive shaft; wherein the engagement system is configured to selectively engage the drill bit to the drive shaft for powered rotation when the drill bit contacts a first material at a first predetermined resistance and to disengage the drill bit from the drive shaft when the drill bit engages a second material at a second predetermined resistance; and wherein the first predetermined resistance is greater than the second predetermined resistance.

In another embodiment, a robot-guided spinal decompression system includes: a surgical tool for use in a system for removing bone from vertebrae to relieve stenosis, the surgical tool comprising: a drill bit having a proximal end and a distal end, a drive shaft having a proximal rod portion and a distal tubular portion, the drill bit and the drive shaft configured to rotate about a horizontal axis in a clockwise direction; and an engagement system disposed between the drill bit and the drive shaft; wherein the engagement system is configured to selectively engage the drill bit to the drive shaft for powered rotation when the drill bit contacts a first material at a first predetermined resistance and to disengage the drill bit from the drive shaft when the drill bit engages a second material at a second predetermined resistance; and wherein the first predetermined resistance is greater than the second predetermined resistance; and a robotic arm; wherein the surgical tool is configured to be controlled by the robotic arm and wherein the robotic arm has a range of motion to facilitate movement of the surgical tool in a predetermined pattern by operation of the robotic arm.

BRIEF DESCRIPTION OF THE DRAWINGS

In the accompanying drawing figures:

FIGS. 6A and B are top sectional views of a portion of a human spine before and after, respectively, a laminotomy procedure;

FIG. 6C is a dorsal view of a portion of a human spine after a laminotomy procedure;

FIG. 20 is a top view of another embodiment of the pressure activated surgical tool.

FIG. 21 is an exploded cut-away top view of the pressure activated surgical tool of FIG. 21.

DETAILED DESCRIPTION OF PREFERRED EMBODIMENTS

Systems and methods for use in spinal decompression procedures are disclosed herein are subject to widely varied embodiments. However, to ensure that one skilled in the art will be able to understand and, in appropriate cases, practice the invention, certain embodiments of the broader invention revealed herein are described below and disclosed by the accompanying drawing figures. The embodiments shown and described are not intended to be limiting.

Figure 1:
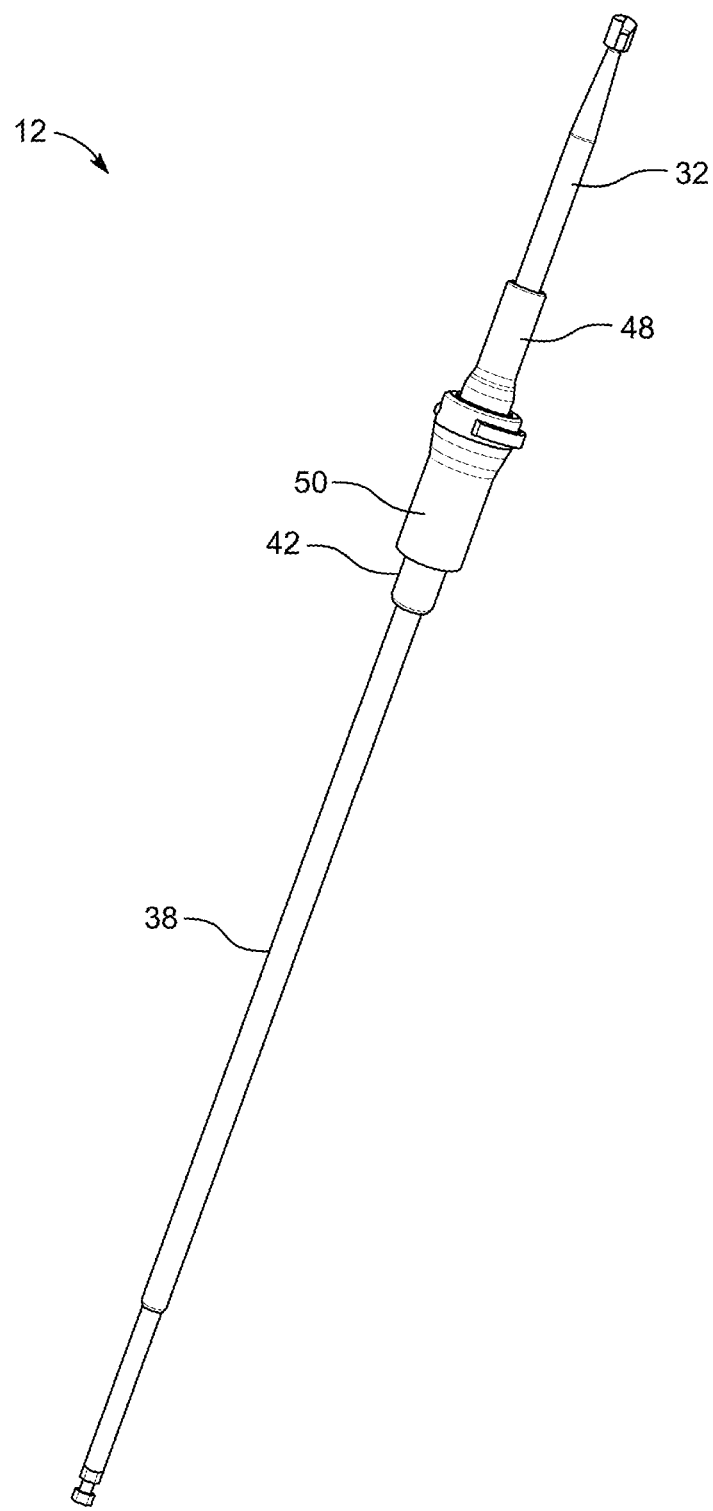
FIG. 1 is a perspective view of a surgical tool for use in a spinal decompression system.
Figure 2:
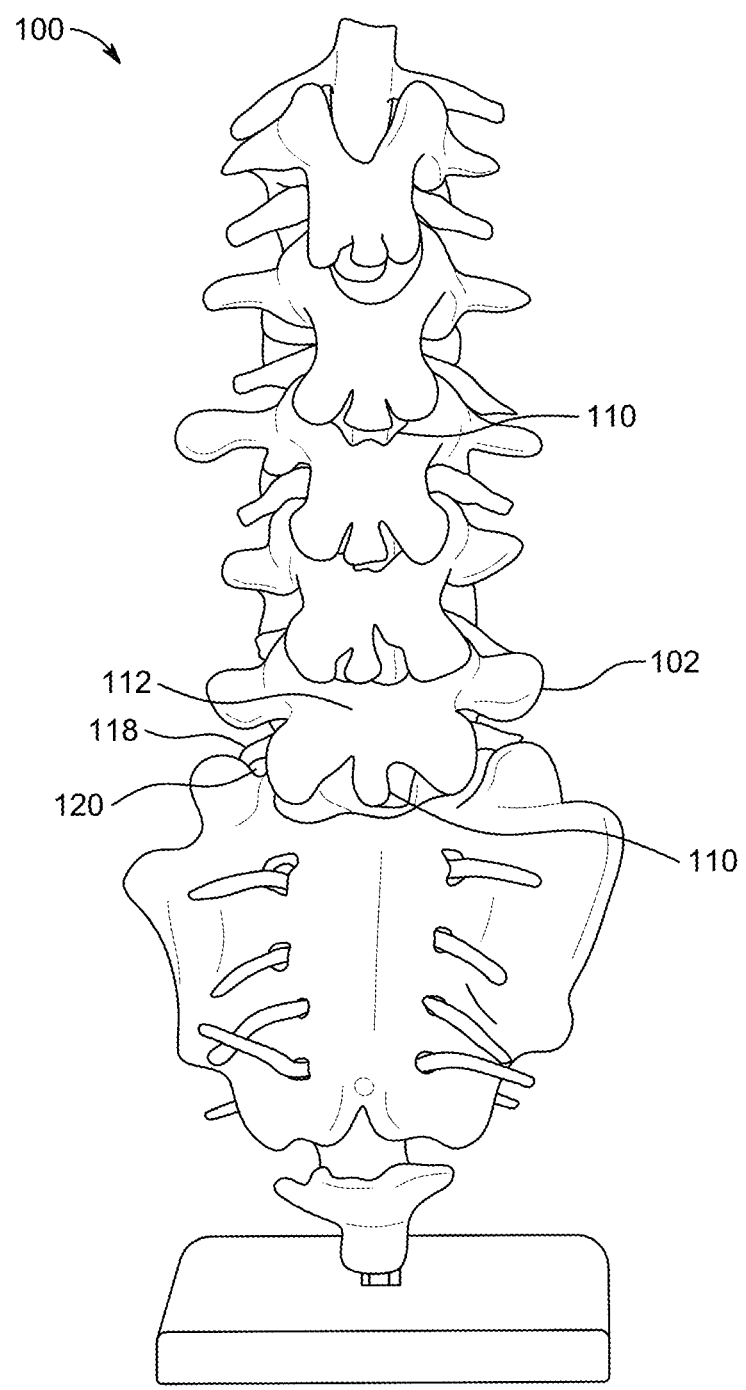
FIG. 2 is a dorsal view of a portion of a human spine.
Figure 3:
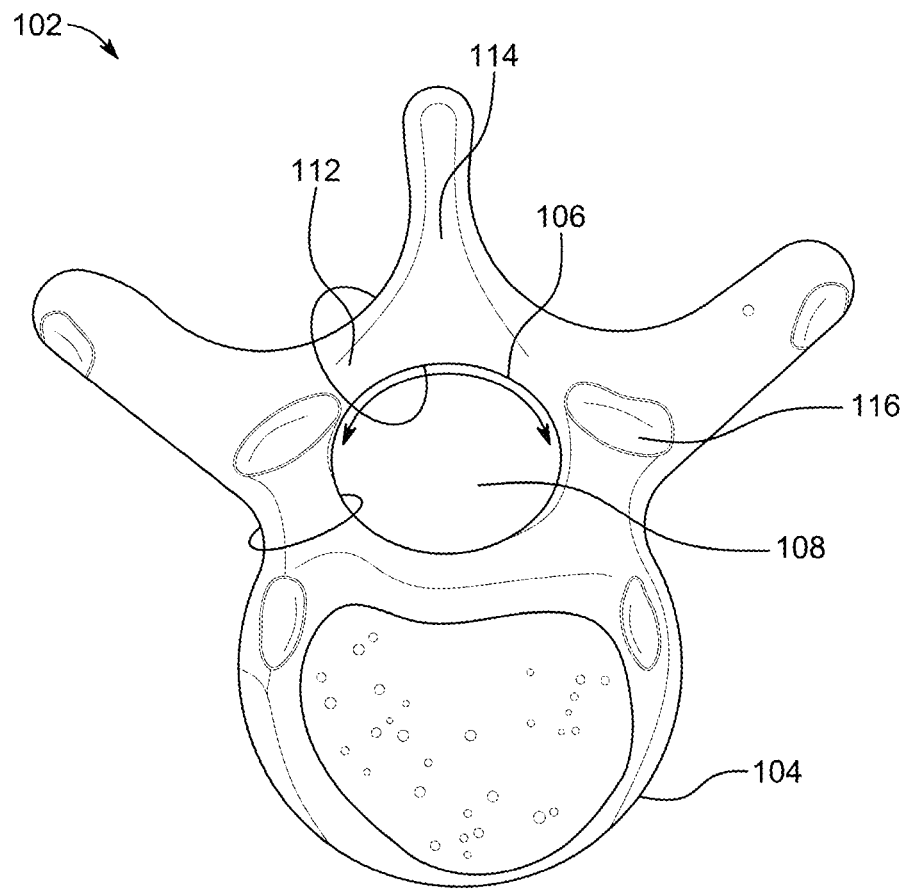
FIG. 3 is a laterally sectioned plan view of a vertebrae of a human spine.
Figure 4:
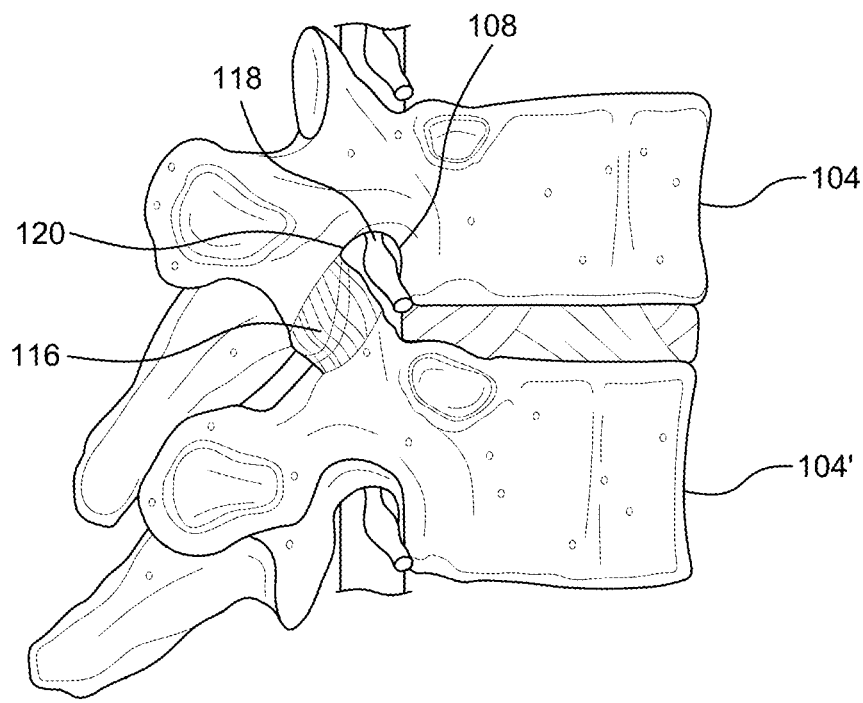
FIG. 4 is a side view of a portion of a human spine including two vertebrae 104 and 104'.
Figure 5:
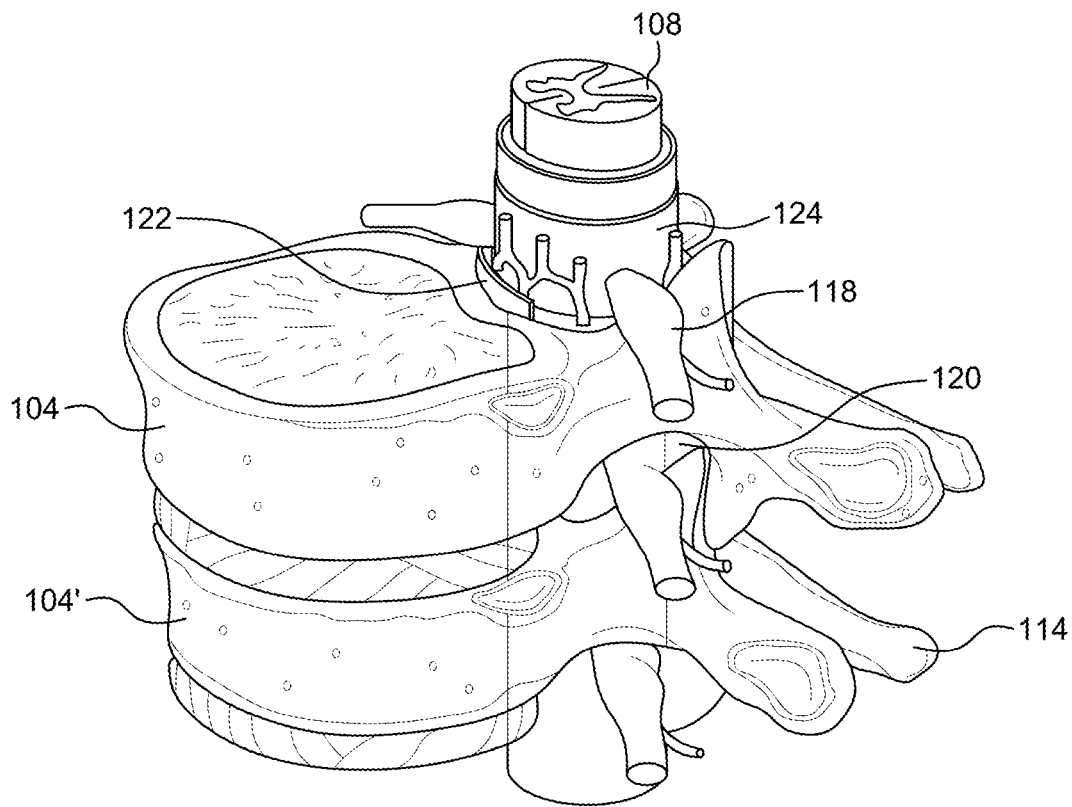
FIG. 5 is a perspective view of a portion of a human spine including two vertebrae 104 and 104'.

Referring now to FIG. 1, a surgical tool 12 for use in spinal decompression procedures is provided. It should be understood that this tool may be used for any procedure in which bone is being removed around a softer material, such as tissue. For example, the surgical tool 12 may also be used to perform a facetectomy in order to perform a interbody fusion. Specifically, the tool 12 can be combined with a robotic navigation system to remove bone at. the facet joint in order to provide access to the disc space. By using the surgical tool 12, the facetectomy can be done percutaneously through a cannula therefore allowing for a more direct exposure to the facet.

Figure 12:
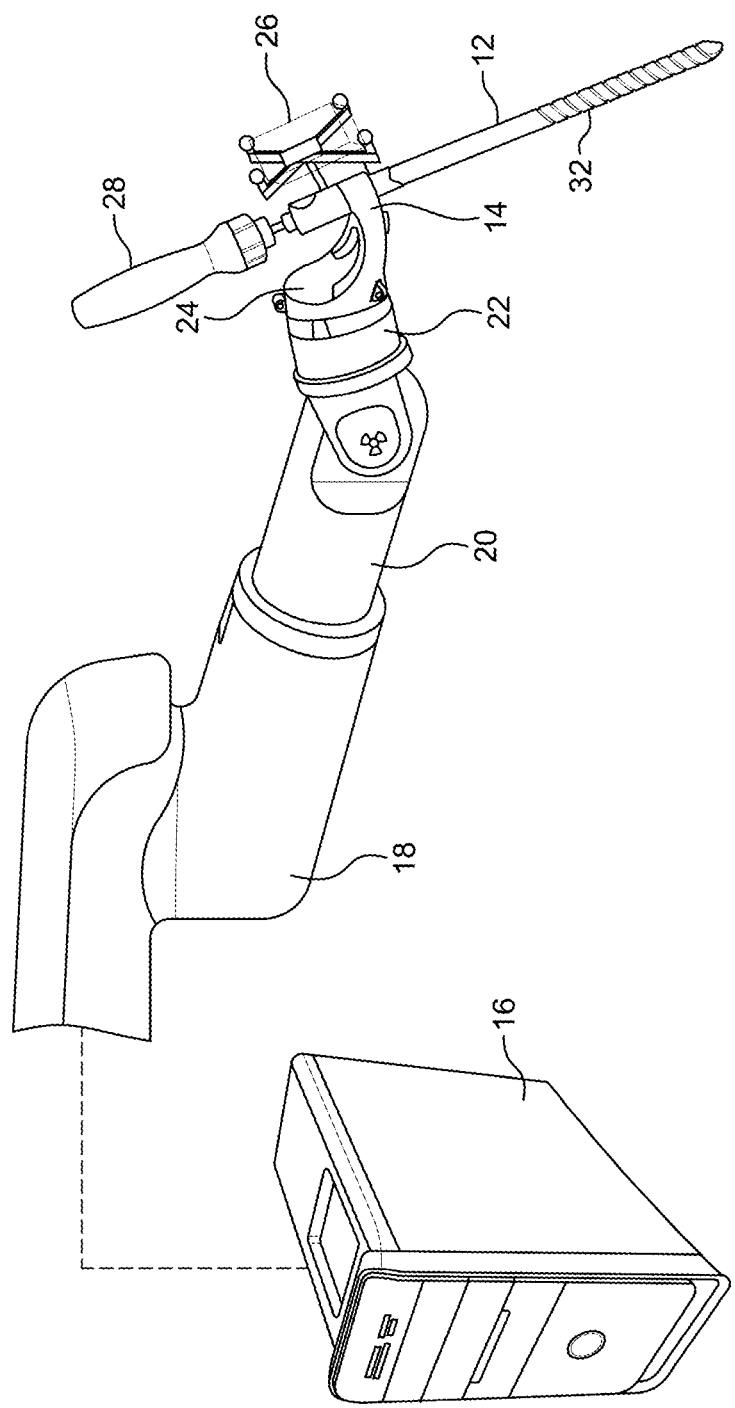
FIG. 12 is a schematic representation of a robotic-assisted system for use in spinal decompression procedures.

In one embodiment, the surgical tool 12 may be operated manually. In another embodiment, the surgical tool 12 may be operated as a part of a spinal decompression system 10 in combination with a robotic arm 14 and a computer system 16, as shown in FIG. 12.

For purposes of illustration, the surgical tool 12 will be described as part of a spinal decompression system 10, which may be configured to enable the performance of laminectomy, laminotomy, and potentially other surgical procedures under robotic guidance with the incorporation of mechanical, electro-mechanical, and overall advancements in methodology and systemic operation. In one embodiment, the robot-guided spinal decompression system 10 permits spinal decompression to be carried out with efficiency and accuracy in an automated manner with reduced reliance on operator skill and dexterity during the course of the spinal decompression procedure.

Figure 7A:
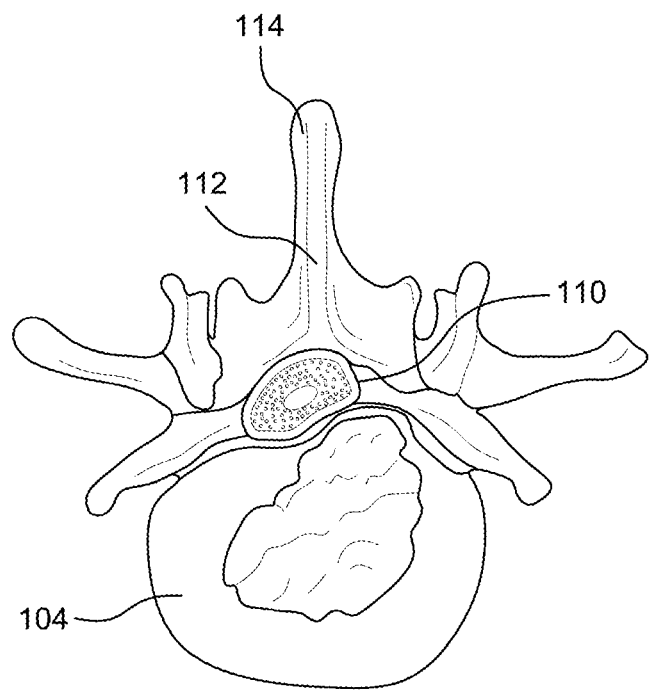
FIGS. 7A and B are top sectional views of a portion of a human spine before and after, respectively, a laminectomy procedure.
Figure 7B:
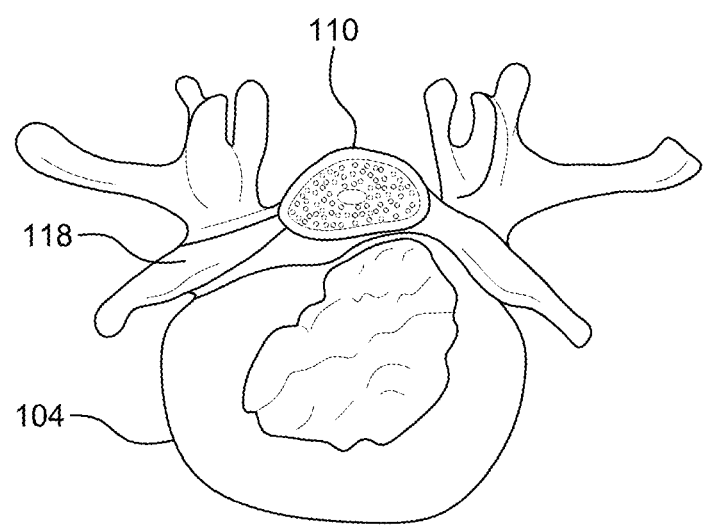
Figure 8A:
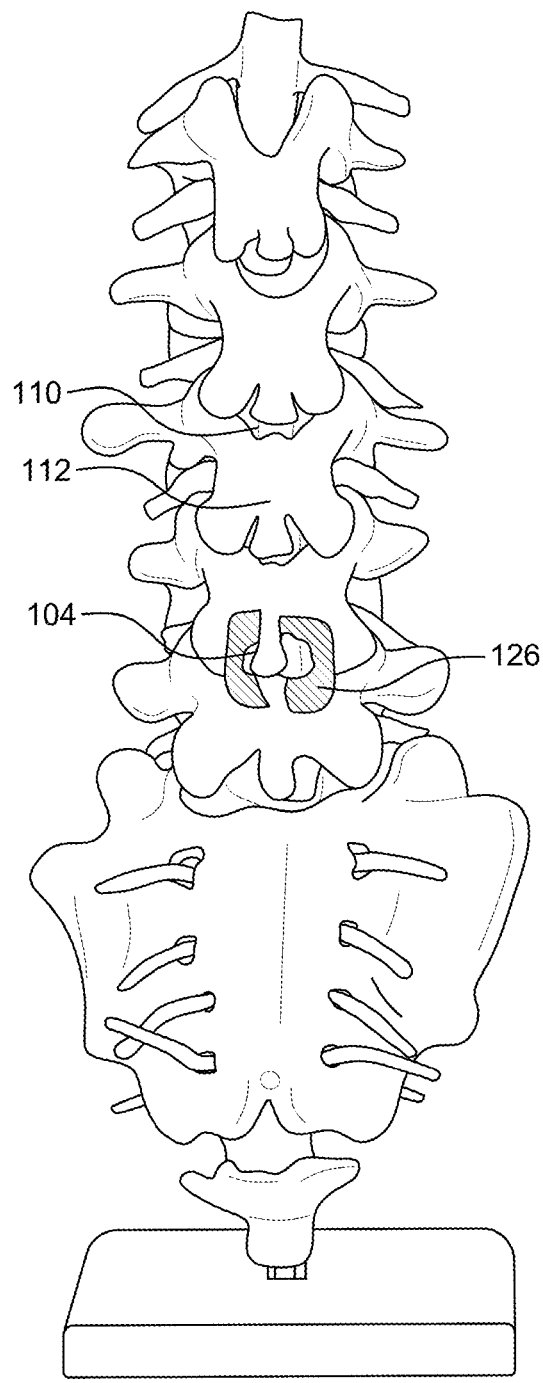
FIG. 8A is a perspective view of a portion of a human spine with a drill pattern for a laminectomy as disclosed herein.
Figure 8B:
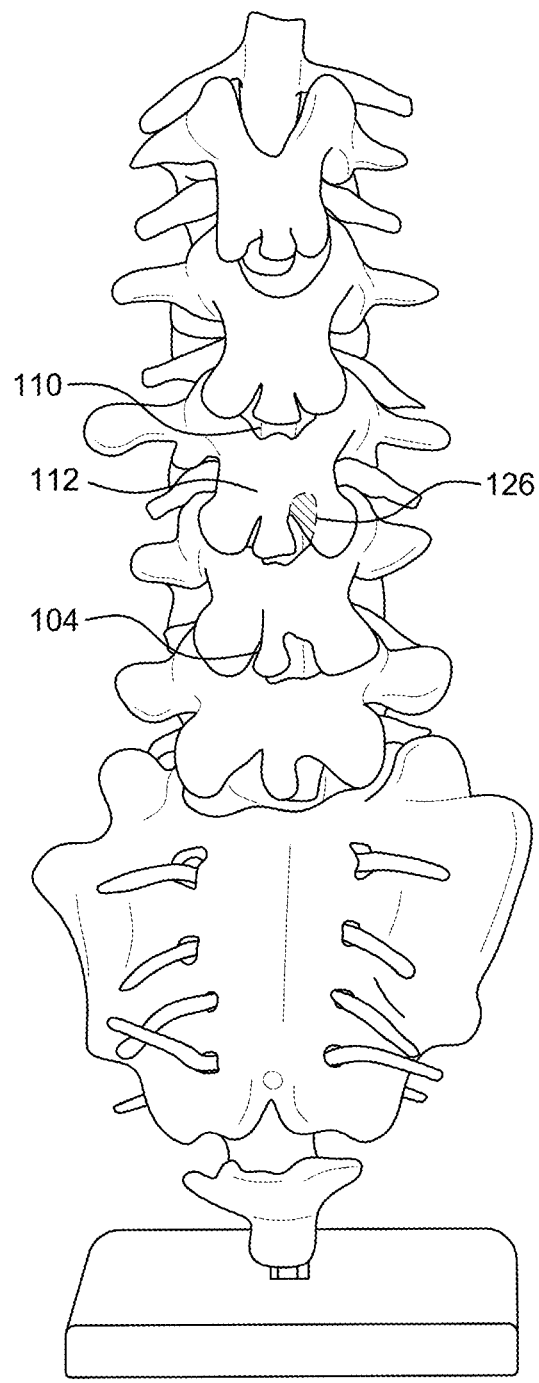
FIG. 8B is a perspective view of a portion of a human spine with a drill pattern for a laminotomy as disclosed herein.

As shown in FIGS. 7A and B, during a lumbar laminectomy, substantially all of the lamina 112 is removed in order to alleviate the cause of a stenosis. However, such extensive material removal exceeds the actual need thereby introducing excessive spinal instability and risk of undue damage to the vertebrae 102, the spinal cord 110, and other aspects of the spine 100.

Figure 11:
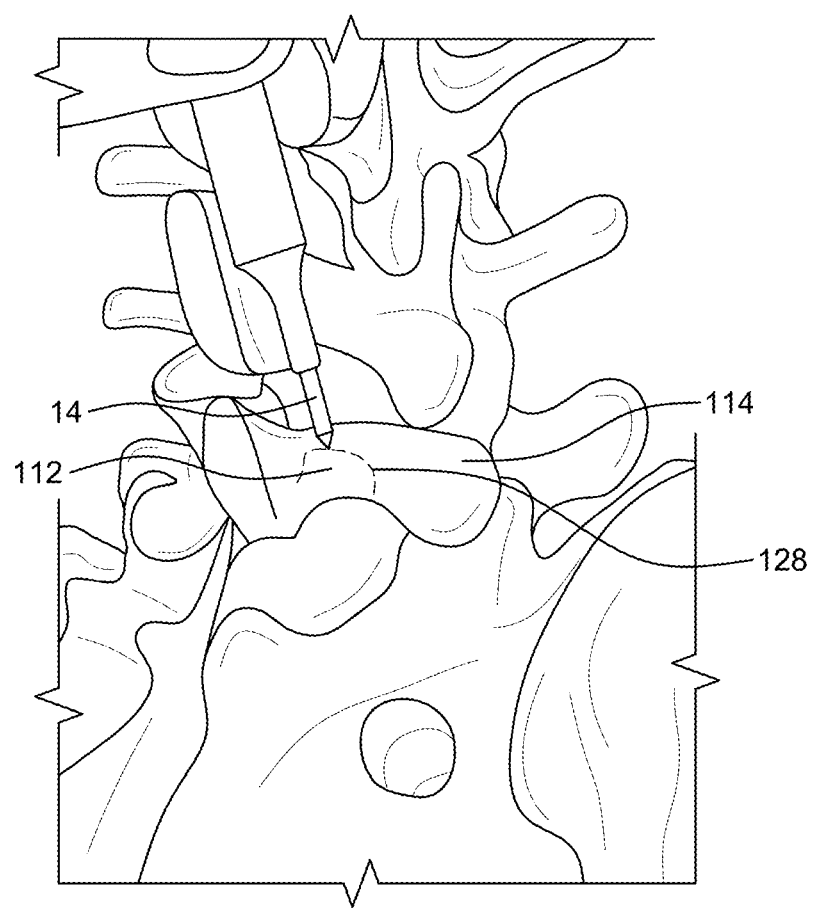
FIG. 11 is a front view of a portion of a human spine showing a drill pattern for partial removal of laminae, as disclosed herein

However, the use of a pressure activated tool in laminectomy procedures as disclosed herein, allows the user to focus on removing only the portion of bone actually causing the spinal stenosis. For instance, as shown in FIG. 11, a targeted laminectomy portion 126 is identified such that only portions of the vertebrae 102 determined to be contributing to the compressive stenosis are designated to be removed. The result of such focused removal leaves more bone intact and, as a result, a more stable structure of the spine 100 and reduced likelihood of damage to the surrounding tissue.

Figure 9:
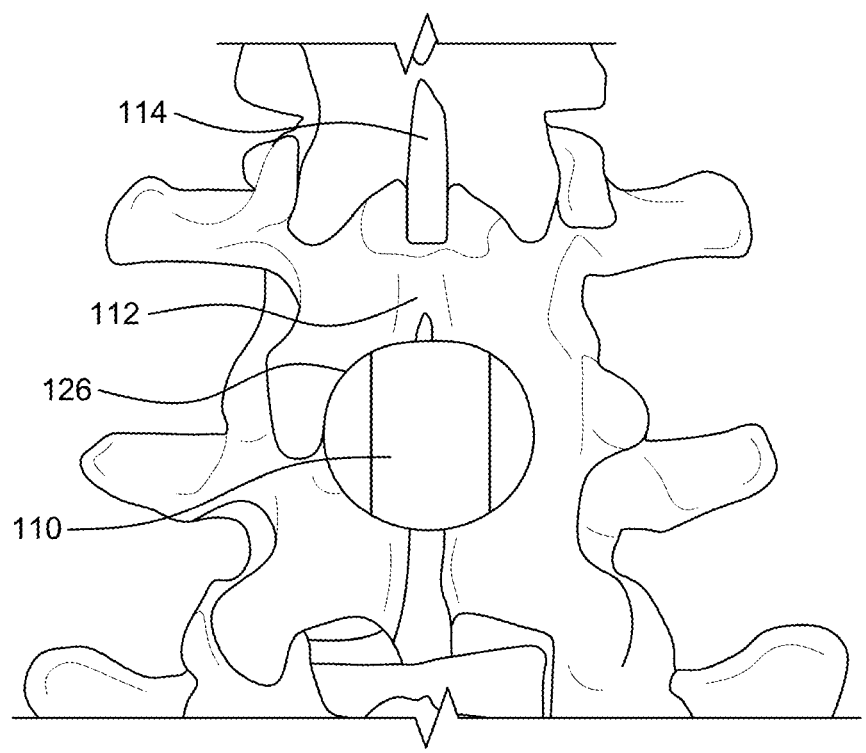
FIG. 9 is a front view of a portion of a human spine after partial removal of the laminae, as disclosed herein.
Figure 10:
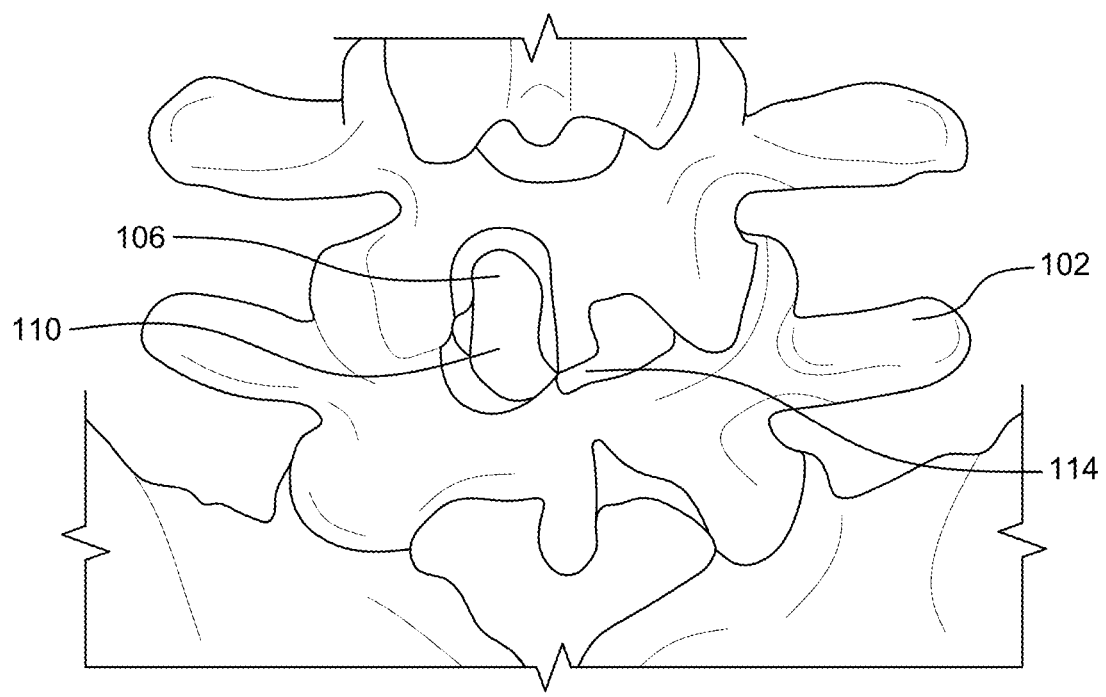
FIG. 10 is a front view of a portion of a human spine after partial removal of laminae, as disclosed herein.

Potential products of the focused removal of constricting portions of vertebrae 102 are depicted in FIGS. 9 and 10. In the non-limiting example of FIG. 9, the targeted laminectomy portion 126 is generally presented as a round area of removed bone material. In FIG. 10, the targeted laminectomy portion 126 is still more focused, including only the portions of lamina 112 determined, such as by pre-surgical planning through a computerized tomography (CT) scan or otherwise, to be contributing to the stenotic constriction.

Based on its shape and localization, the focused laminectomy can be referred to as a pothole laminectomy. With the pothole laminectomy, the entire lamina 112 is not removed. Instead, a more precise procedure is undertaken with only the portion of the lamina 112 (and potentially the spinous process 114) identified as causing the stenosis, being removed while the remainder of the vertebrae 102 is preserved.

With further reference to FIGS. 13 through 18, for example, a pressure activated surgical tool 12 can be employed as a carving instrument to remove what has been identified as stenotic bone of a targeted laminectomy 126. The surgical tool 12 can operate in a drill pattern 128 (as shown in FIG. 11), which can be predefined. While the drill pattern 128 could be followed manually, embodiments of the present invention contemplate an automated traversing of the drill pattern 128 under robotic control.

As illustrated in FIG. 12, for example, the surgical tool 12 can be retained at the distal end of a robotic arm 14. The surgical tool 12 can thus be manipulated robotically by the robotic arm 14. The robotic arm 14 can have multiple degrees of freedom to permit adjustment of the location and orientation of the surgical tool 12 within the range of motion of the robotic arm 14. In the embodiment depicted, the robotic arm 14 has a proximal portion 18 pivotable about a vertical axis, a first intermediate portion 20 extendible and retractable in relation to the proximal portion 18, a second intermediate portion 22 pivotable about a lateral axis in relation to the first intermediate portion 20, and a distal portion 24 pivotable about a longitudinal axis in relation to the second intermediate portion 22. Under this construction, the position and orientation of the surgical tool 12 can be adjusted substantially infinitely within the range of motion of the robotic arm 14.

Actuation and movement of the robotic arm 14 and the surgical tool 12 can be partially or completely automated. Control of the robotic arm 14 and the surgical tool 12 can, in certain practices, be performed by commands received from one or more computers 16, possibly based on image information obtained by an image acquisition device 26, such as a camera, and image information obtained by prior analysis. The computer 16 can be local to the robotic arm 14 and the surgical tool 12, or it could be remotely located. Where an image acquisition device 26 is employed, it could be retained by the robotic arm 14 as shown in FIG. 12 or otherwise disposed to perceive the relative position and operation of the robotic arm 14, the surgical tool 12, and the area of the operation.

The surgical tool 12 can be selectively powered by a rotary power system 28 that can be retained locally to the surgical tool 12 as in FIG. 12 or remotely. Through automation, manual control, or some combination thereof, the surgical tool 12 can be caused to remove bone material along the drill pattern 128, whether by repeated adjacent drilling, by lateral movement, or by some other movement or combination thereof. The surgical tool 12 can thus be manipulated under computer control to traverse the predetermined pathway of the drill pattern 128 to achieve a desired surgical result, which in this non-limiting example is a pothole laminectomy.

As referenced hereinabove, it is contemplated that the surgical path of the drill pattern 128 could be determined by pre-surgical planning. For instance, a patient may undergo one or more computerized scans, such as computerized tomography (CT) scans, to determine the vertebrae 102 and the particular portion of the vertebrae 102 causing the stenosis. Based on the computer data derived from the scanning, a surgeon can plan the laminectomy, and the required drill pattern 128 to establish the same can be established automatically by computer 16, manually, or by some combination of the two or in another manner. The resulting surgical plan retained in electronic memory can then be electronically conveyed to the computer-controlled robotic system shown and described herein. Prior to surgery, predetermined reference points on the patient can be established and confirmed. Then, the robotic arm 14 and the surgical tool 12 can be actuated and controlled by computer 16 to perform the planned laminotomy or laminectomy according to the surgical plan.

With continued reference to FIG. 12, the depicted embodiment of the surgical tool 12 incorporates an engagement system 30. In one embodiment, the engagement system 30 may be a pressure activated engagement system 30. The engagement system 30 is operative to engage a drill bit 32 (or other suitable implement used for bone removal or sculpting) for powered rotation when the drill bit 32 engages a first material 34 of a first predetermined resistance, such as bone, and to disengage the drill bit 32 from rotational power when the bit 34 engages a second material 36 at a second predetermined resistance. The engagement system 30 could be operative to engage and disengage the drill bit 32 relative to powered rotation based on resistance longitudinally, axially, laterally, rotationally, or in some other direction or combination of directions. While non-limiting embodiments of engagement systems 30 disclosed herein are operative to engage and disengage a drill bit 32 based on axial or longitudinal resistance, engagement systems 30 are contemplated and within the scope of the invention where lateral, longitudinal, axial, and/or rotational resistance produces an engagement or disengagement of the drill bit 32.

Under the disclosed constructions, when the drill bit 32 is engaged with the bone of the lamina 112 of a vertebra 102 (i.e. a first material 34 having a first predetermined resistance), for instance, the drill bit 32 can be rotated. However, when the drill bit 32 passes through the bone to reach the underlying tissue (i.e. a second material 36 at a second predetermined resistance), rotational power to the bit 34 is automatically terminated, thereby preventing injury to the relatively soft tissue and neural elements (the second material 36) within the vertebral foramen 108 and elsewhere. It should be understood that the first and second predetermined resistances can be adjusted based on the intended use and the physical attributes of the patient, such as bone density.

Accordingly, working in combination, robotic control and the engagement system 30, potentially in further combination with image guidance provided by one or more image acquisition devices 26, enables the removal of bone causing stenosis while minimizing the risk of injury to the underlying and adjacent soft tissue and neural elements. The surgical tool 12 can be operated to drill adjacent holes or to travel laterally in relation to bone along a predetermined, programmed trajectory to create the predetermined laminotomy or laminectomy along the predetermined drill pattern 128. Improved accuracy, consistency, uniformity, and a higher success rate can be achieved in comparison to traditional laminotomy and laminectomy procedures. With the engagement system 30, the robot-guided spinal decompression system 10 thus can engage and cut when encountering bone and disengage and stop cutting before penetrating the tissue, including the nervous layer, underneath and adjacent to the bone. Accuracy and consistency are improved and the risk of surgical error is minimized.

In one embodiment, the engagement system 30 could be mechanical, electro-mechanical, electronic, or some other operative engaging mechanism or combination thereof. By way of example and not limitation, the engagement system 30 could be embodied as a clutch mechanism, a mechanical, electro-mechanical, or electronic pressure sensor, a bone or tissue or material detection system, or in any other manifestation operative to cease or prevent rotation of the drill bit 32 on encountering tissue or neural material but to permit rotation of the drill bit 32 on encountering bone.

During operation of the robot-guided spinal decompression system 10, the surgical tool 12 can be automatically repositioned, such as by retraction and alignment with a subsequent drilling location or withdrawal to a storage or non-use position, on a disengagement of the surgical tool 12 by operation of the engagement system 30. The automatic repositioning can be induced, for example, by the engagement system 30 in combination with the robotic arm 14 under control of the computing system 16.

Figure 13:
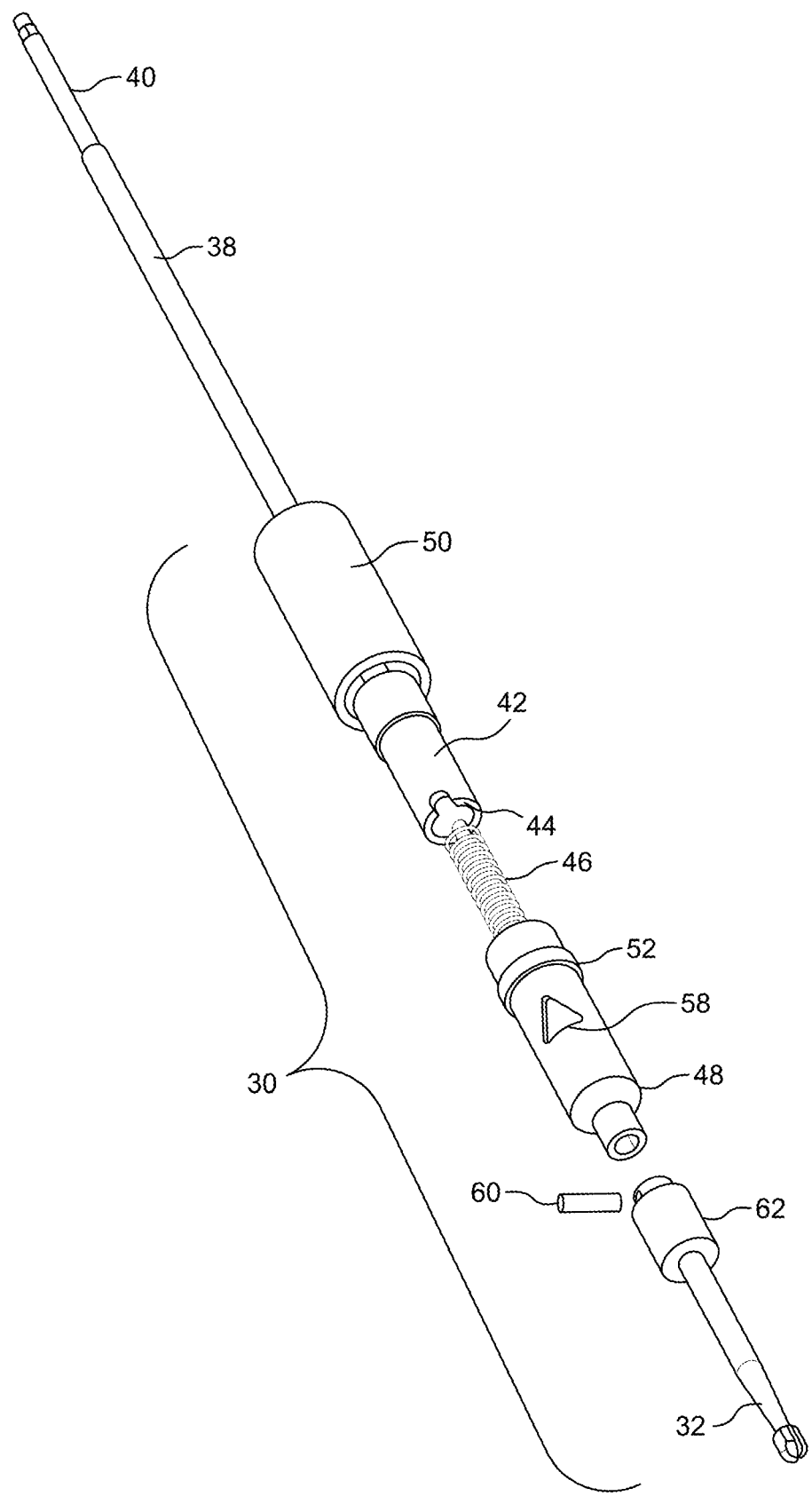
FIG. 13 is an exploded view in side elevation of a pressure-activated surgical tool.

The structure and operation of a surgical tool 12 incorporating a pressure engagement system 30 according to the invention can be better understood with reference to FIGS. 13 through 18. With reference to FIG. 13, in one embodiment, the surgical tool 12 includes an engagement system 30, a drill bit 32 having a proximal end and a distal end, and a drive shaft 38. The drive shaft 38 has a proximal rod portion 40 and a distal tubular portion 42 that terminates in a contoured formation 44.

Figure 13A:
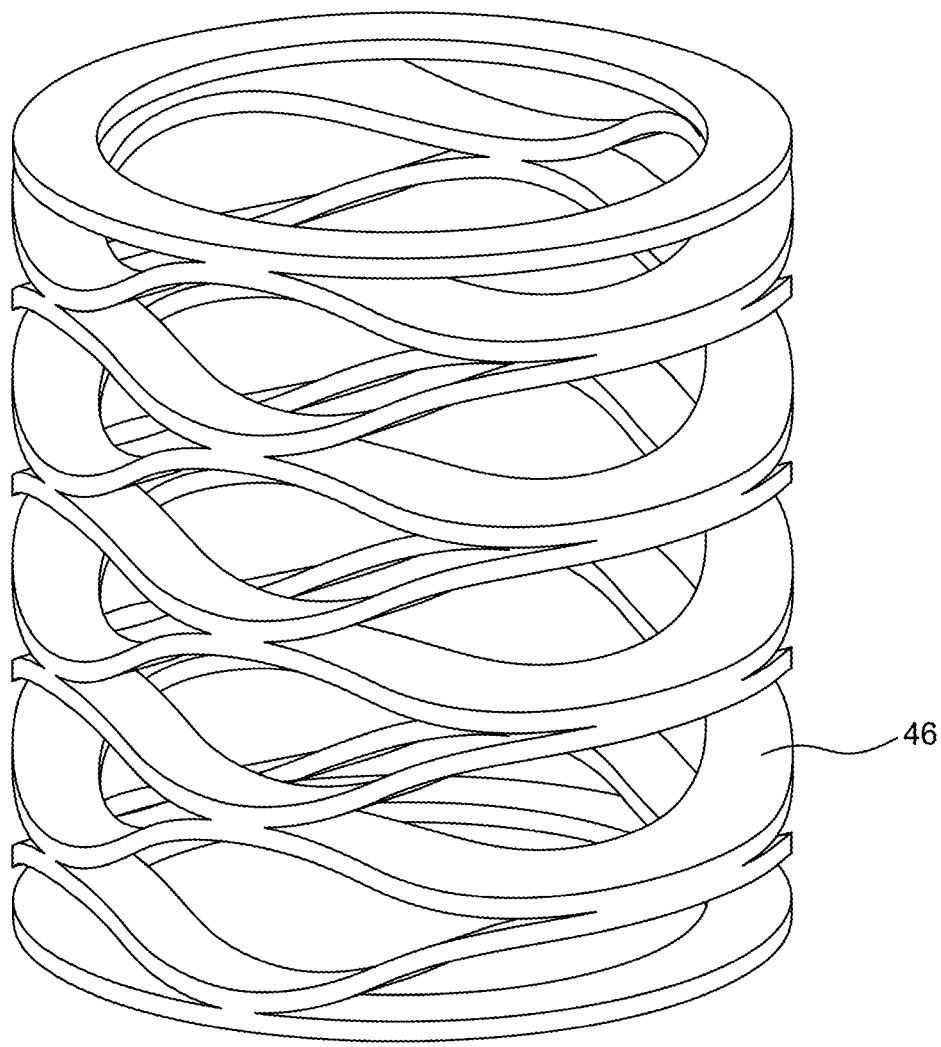
FIG. 13A is a front perspective view of a wave spring suitable for use with the pressure-activated surgical tool.
Figure 14:
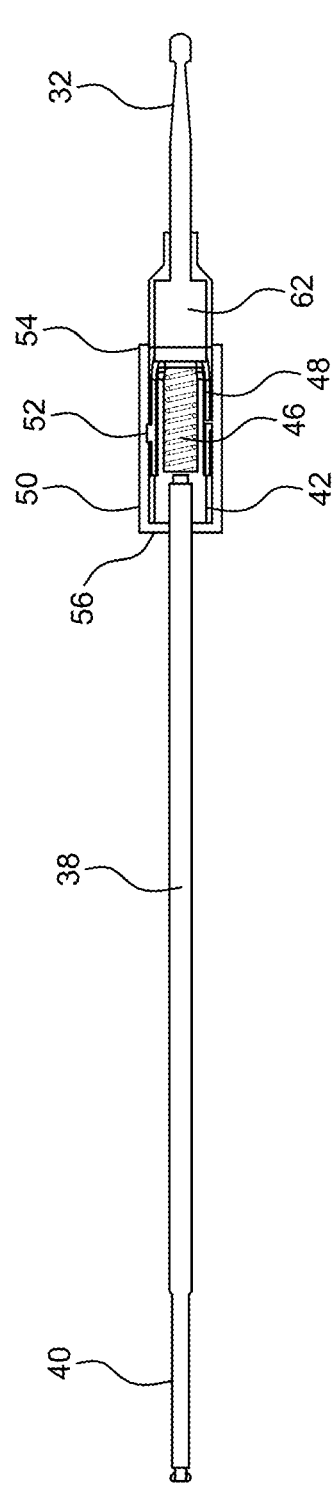
FIG. 14 is a partially sectioned side view of a pressure-activated surgical tool, as disclosed herein.
Figure 15:
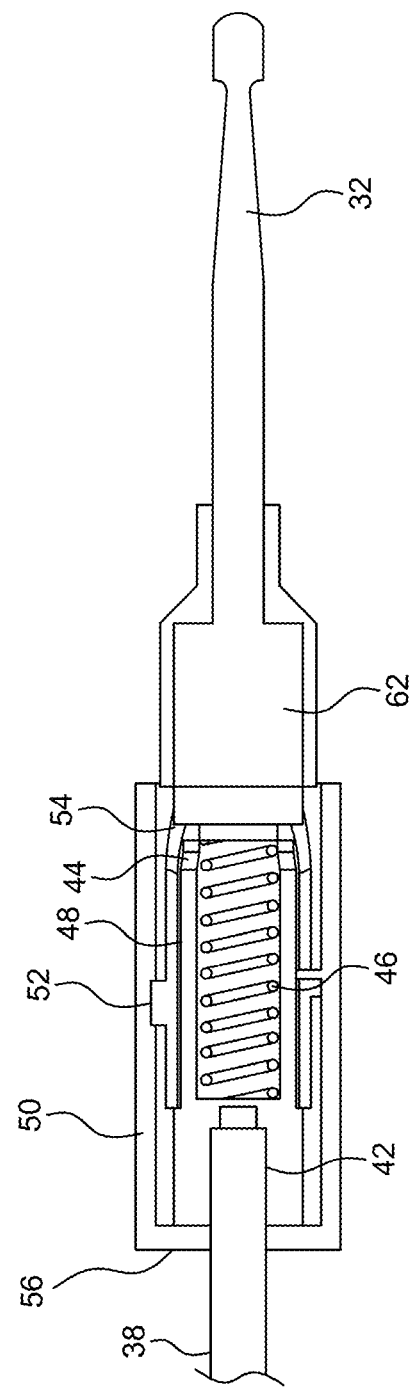
FIG. 15 is an amplified partially sectioned view in side elevation of the pressure-activated surgical tool of FIG. 14.
Figure 19:
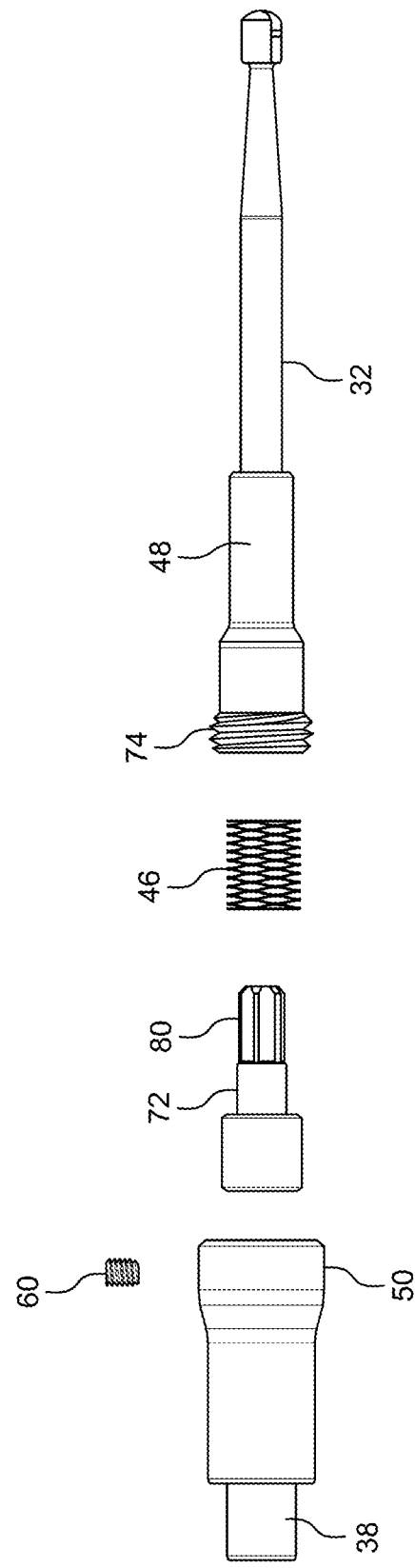
FIG. 19 is an amplified side view of another embodiment of the pressure-activated surgical tool.

The proximal rod portion 40 of the drive shaft 38 is configured to engage a connection of the rotary power system 28 of, for instance, a robotic drilling platform. In one embodiment, a first compression spring 46 is matingly received into the distal tubular portion 42 of the drive shaft 38. The spring rating of the compression spring 46 will largely control the amount of resistance required for the drill bit 32 to be engaged (the first predetermined resistance) and likewise, will largely control the level of resistance at which the drill bit 32 will disengaged (second predetermined resistance). In one embodiment, the compression spring 46 may be a standard coil design. In another embodiment, as shown in FIGS. 13A and 19, the spring 46 may be a wave spring.

In yet another embodiment, the compression spring 46 may be replaced by an electronic pressure sensor or strength gauge that will similarly be used to control the amount of resistance (or pressure) required to engage and disengage the drill bit 32. One example of a suitable electronic sensor may be a pressure transducers such as potentiometric pressure sensors, inductive pressure sensors, capacitive pressure sensors, piezoelectric pressure sensors, strain gauge pressure sensors, and variable reluctance pressure sensors.

The distal tubular portion 42 of the drive shaft 38 is, in turn, matingly received into an inner housing 48. An outer housing 50 is received over the proximal portion of the inner housing 48. The inner and outer housings 48 and 50, the first compression spring 46, and the distal tubular portion 42 of the drive shaft 38 are retained under compression in the assembled configuration of, for example, FIGS. 14 and 15 by the combined effects of a ridge 52 on the outer surface of the inner housing 48, a ledge 54 at a distal end of the outer housing 50, and a cap portion 56 proximally disposed on the outer housing 50. The inner housing 48, the outer housing 50, the drive shaft 38, and the drill bit 32 are concentrically disposed.

A contoured aperture 58 is disposed through the cylindrical wall of the inner housing 48, and a pin 60 projects laterally from a base portion 62 of the drill bit 32 to be received through the contoured aperture 58. The aperture 58 has a greater component along the longitudinal axis of the surgical tool 12 than does the pin 60, and the base portion 62 of the drill bit 32 is slidably engaged with the inner housing 48.

Figure 16:
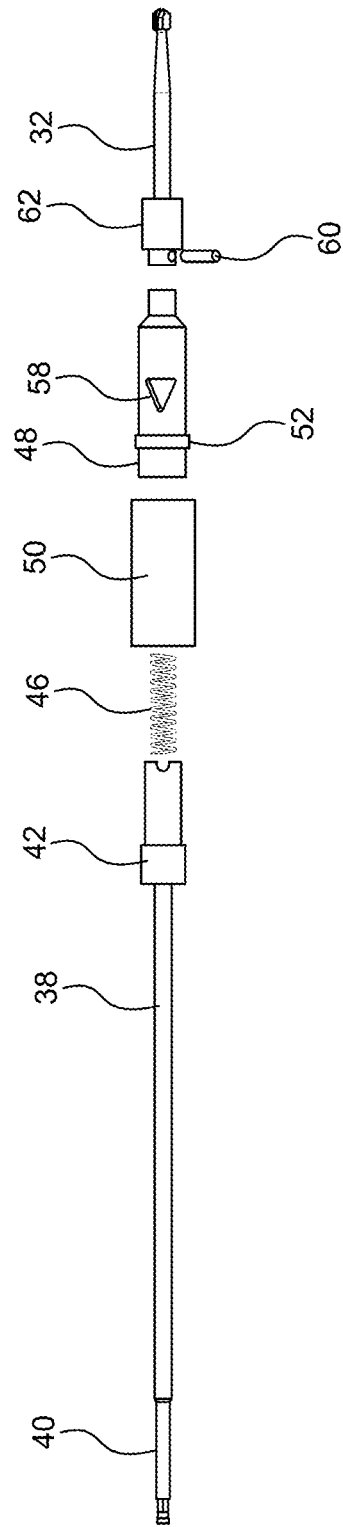
FIG. 16 is an exploded view in side elevation of the pressure-activated surgical tool.
Figure 17:
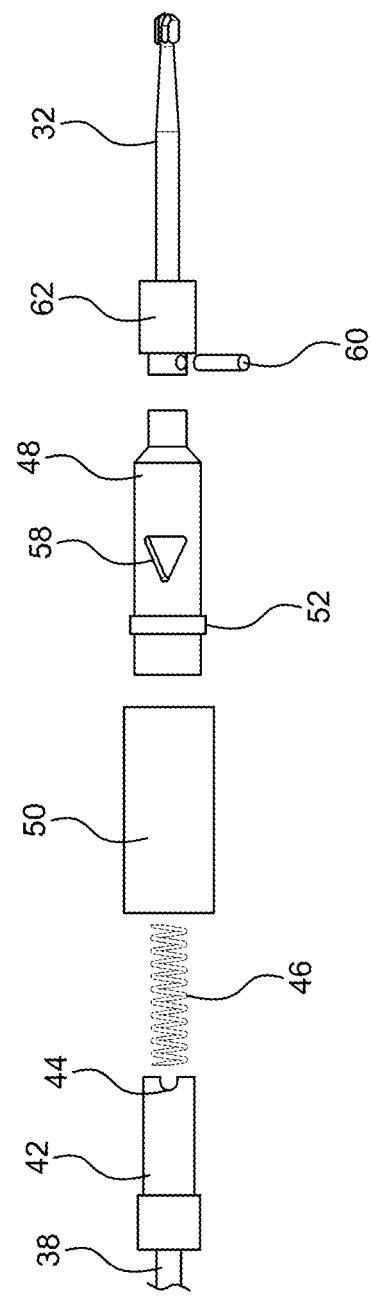
FIG. 17 is an amplified exploded view in side elevation of the pressure-activated surgical tool.
Figure 18:
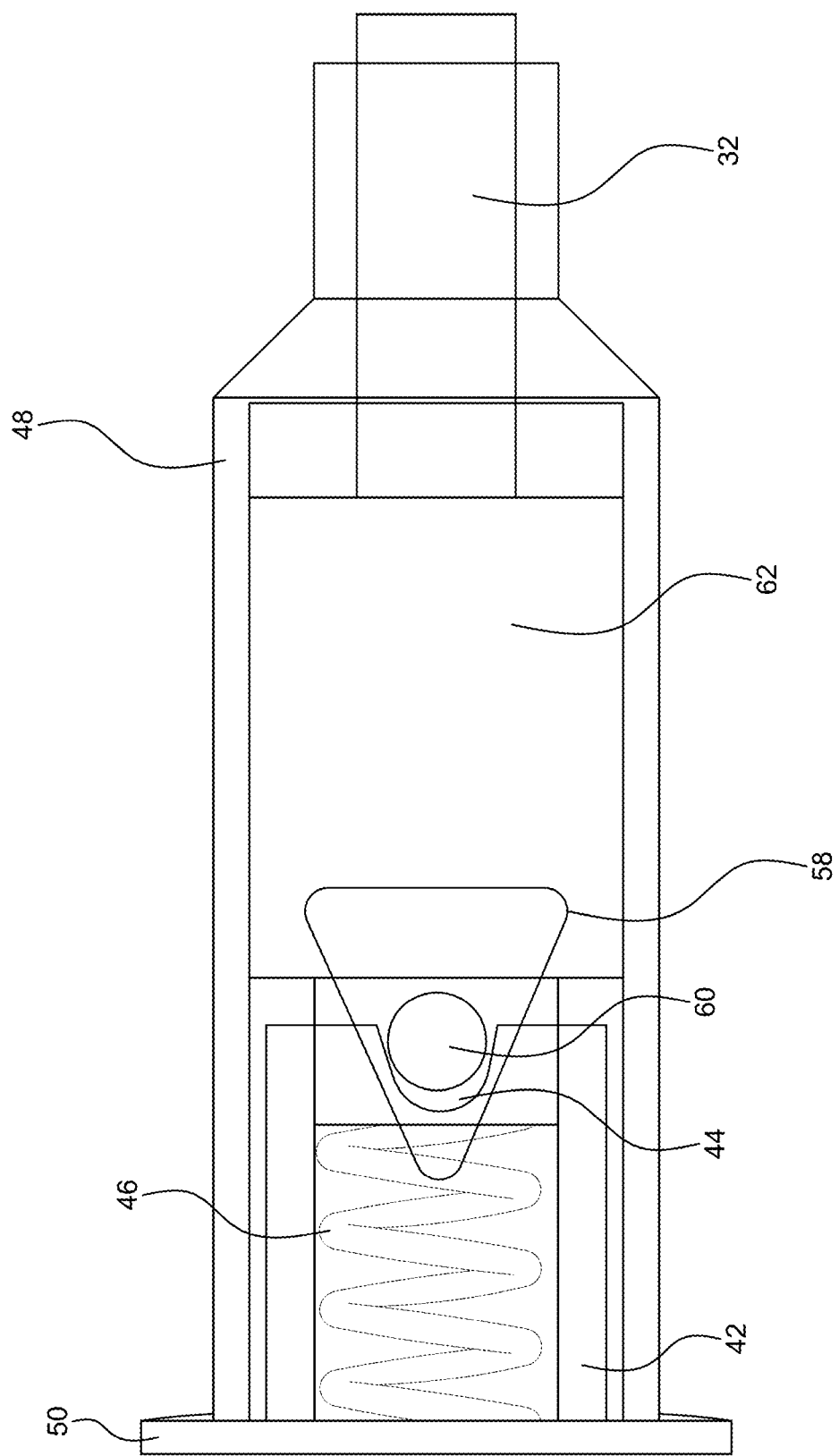
FIG. 18 is a partially sectioned view in side elevation of the engaging portion of the pressure-activated surgical tool.

As can be perceived by reference to FIGS. 16-18, when sufficient axial compressive force is applied to the drill bit 32, the base portion 62 of the drill bit 32 will tend to compress the first compression spring 46 and move longitudinally deeper within the inner housing 48. As the base portion 62 moves within the inner housing 48, the pin 60 will move proximally in the longitudinal direction within the contoured aperture 58. When the base portion 62 is moved sufficiently, the contoured formation 44 at the distal end of the drive shaft 38 engages the pin 60. When the drive shaft 38 is in rotation, it will then rotate the drill bit 32 to permit drilling.

However, when the axial force applied to the drill bit 32 is reduced to below the expansive force of the first spring 46, the base portion 62 of the drill bit 32 will be released distally within the inner housing 48 and the pin 60 will move distally in the longitudinal direction within the contoured aperture 58. When the base portion 62 is moved sufficiently away from the drive shaft 38, the contoured formation 44 at the distal tubular portion 42 of the drive shaft 38 will disengage the pin 60, and rotational power to the drill bit 32 will be terminated automatically.

Figure 23:
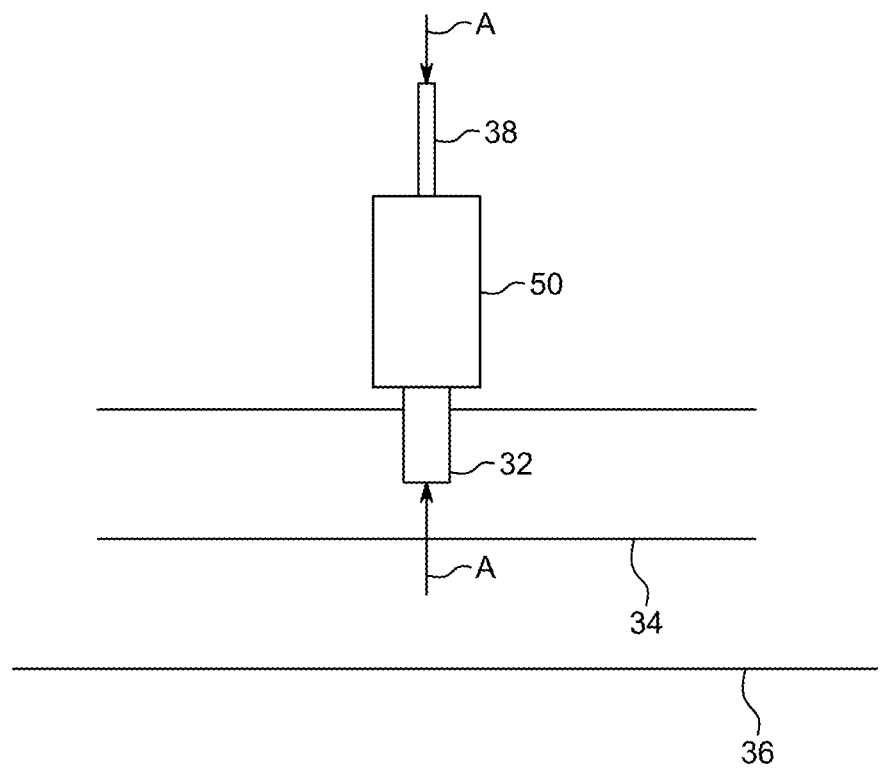
FIG. 23 is a schematic view in side elevation of the pressure-activated surgical tool drilling through a first material.
Figure 24:
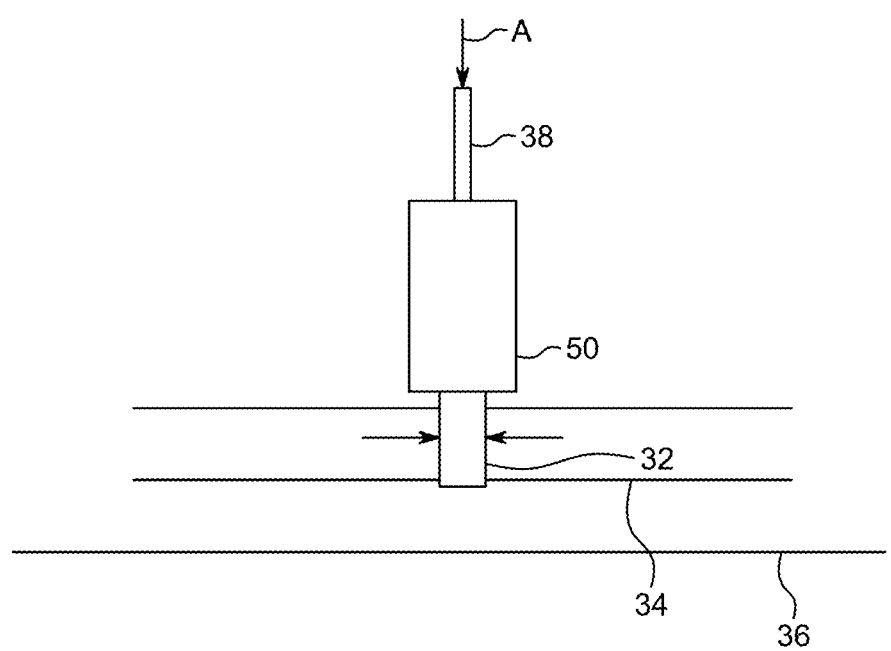
FIG. 24 is a schematic view in side elevation of the pressure-activated surgical tool after drilling through a first material and reaching a second material.

Under this construction, the drill bit 32 may rotate at a speed of between 5,000 and 80,000 RPM. In one embodiment, the force required to engage the first compression spring 46 is about 1 pound-force (lbf) to about 20 lbf. As is shown in FIGS. 23 and 24, as the drill bit 32 encounters sufficient resistance (i.e. a first predetermined resistance), such as when the drill bit 32 encounters the bone of the laminae (i.e. the first material 34), axial force A can be applied sufficient to compress the first compression spring 46 and to engage the drill bit 32 with the drive shaft 38. Rotation of the drive shaft 38 will then induce rotation of the drill bit 32 to permit cutting of the bone 106.

However, when the first material 34 is pierced and softer tissue or neural material (i.e. the second material 36) is encountered, the reduced longitudinal resistance A (or second predetermined resistance) will be overcome by the expanding force of the first compression spring 46 thereby disengaging the drill bit 32 from the drive shaft 38 so that even continued rotation of the drive shaft 38 will not induce further rotational cutting by the drill bit 32.

The robot-guided spinal decompression system 10 so disclosed can be employed to perform laminotomies and laminectomies under robotic guidance with enhanced precision and minimized risks of injury to the spinal cord 110 and other tissue underlying and adjacent to vertebrae 102. Under computer 16 guidance, the robotic arm 14 and the surgical tool 12 can perform drilling operations along a predetermined robotic drill pattern 128 through the lamina 112 and other bony portions to remove only bone contributing to spinal stenosis while sparing bony portions, facet joints 116, ligaments 122, and other bodily components not contributing to stenosis. With that, the effectiveness and precision of laminotomies and laminectomies can be improved while impact on the strength and stability of the structure of the spine 100 can be minimized.

In another embodiment, as shown and described in FIGS. 19, 20, and 21, the surgical tool 12 further includes a drive shaft extension 72 with an engagement end 80 that is disposed around the distal tubular portion 42 of the drive shaft 38. The engagement end 80 is configured to mate with a correspondingly shaped pocket 78 within the inner housing. Therefore, when the spring 46 is compressed by force applied by the first material, the engagement end 80 is moved longitudinally in to and fitted within the corresponding pocket 78 to engage the drill bit 32.

In addition, the proximal end of the inner housing 48 may include a threaded portion 74 that is configured to attach to a threaded portion 76 on the distal end of the outer housing 50. This allows the user to change the spring 46, in order to customize the resistance required to engage the drill bit 32. In this embodiment, the pin 60 extends through an opening in the distal end of the outer housing 50 and fits within an opining 82 within the threaded portion 74 of the inner housing.

While a mechanical engagement system 30 is often shown and described herein, it will be understood that other engagement systems and combinations of engagement systems and mechanisms would be possible and within the scope of the invention. By way of example, it would be possible to have a longitudinal force sensor operably associated with the surgical tool 12 to sense the resistive force experienced by the drill bit 32. The engagement system 30 can be operative to permit rotation of the drill bit 32 when resistance in excess of a predetermined resistance is encountered and to prevent rotation of the drill bit 32 when resistance below the predetermined resistance is encountered.

Figure 22A:
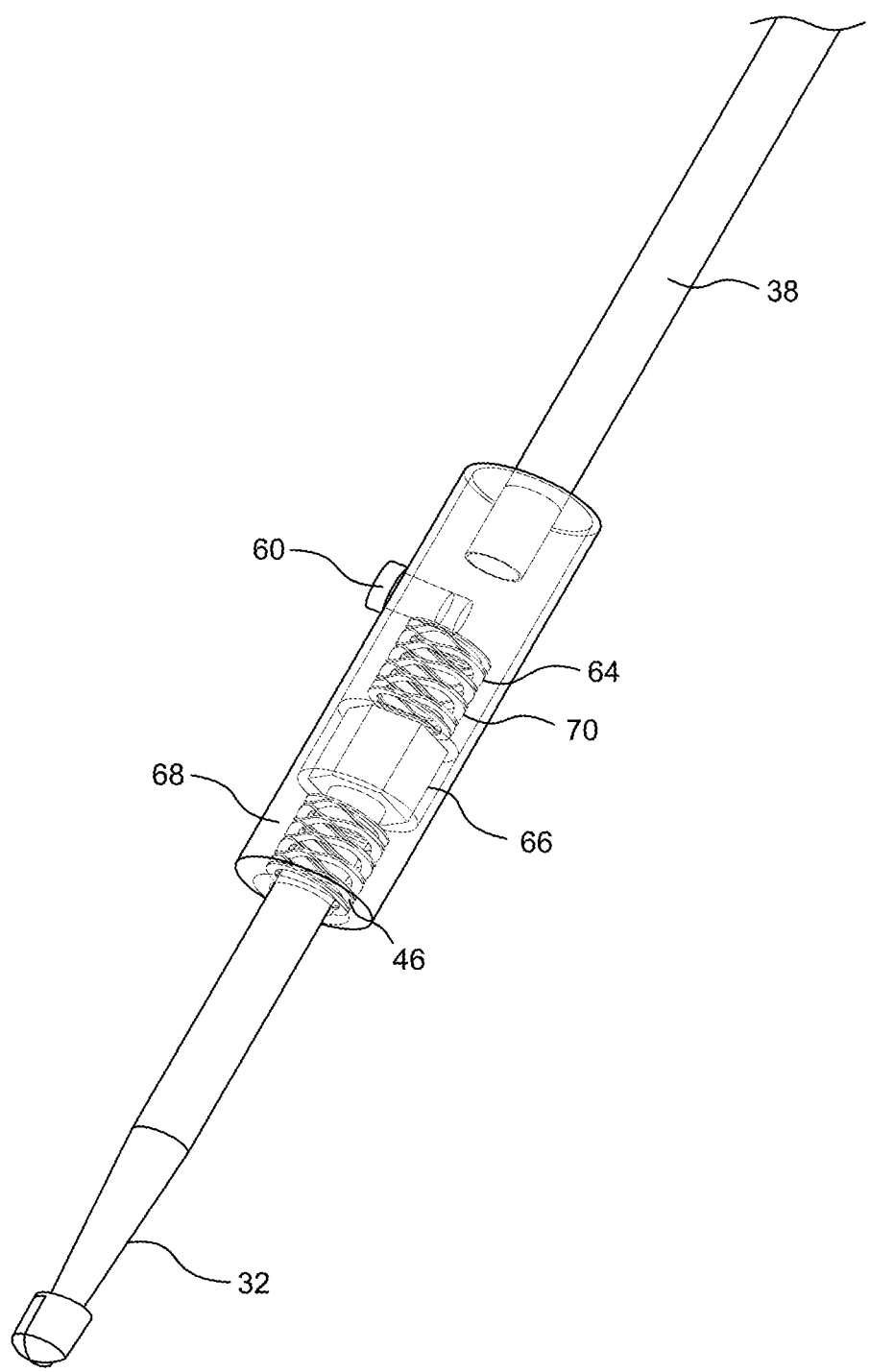
FIG. 22A is a perspective view of another embodiment of a pressure-activated surgical tool.
Figure 22B:
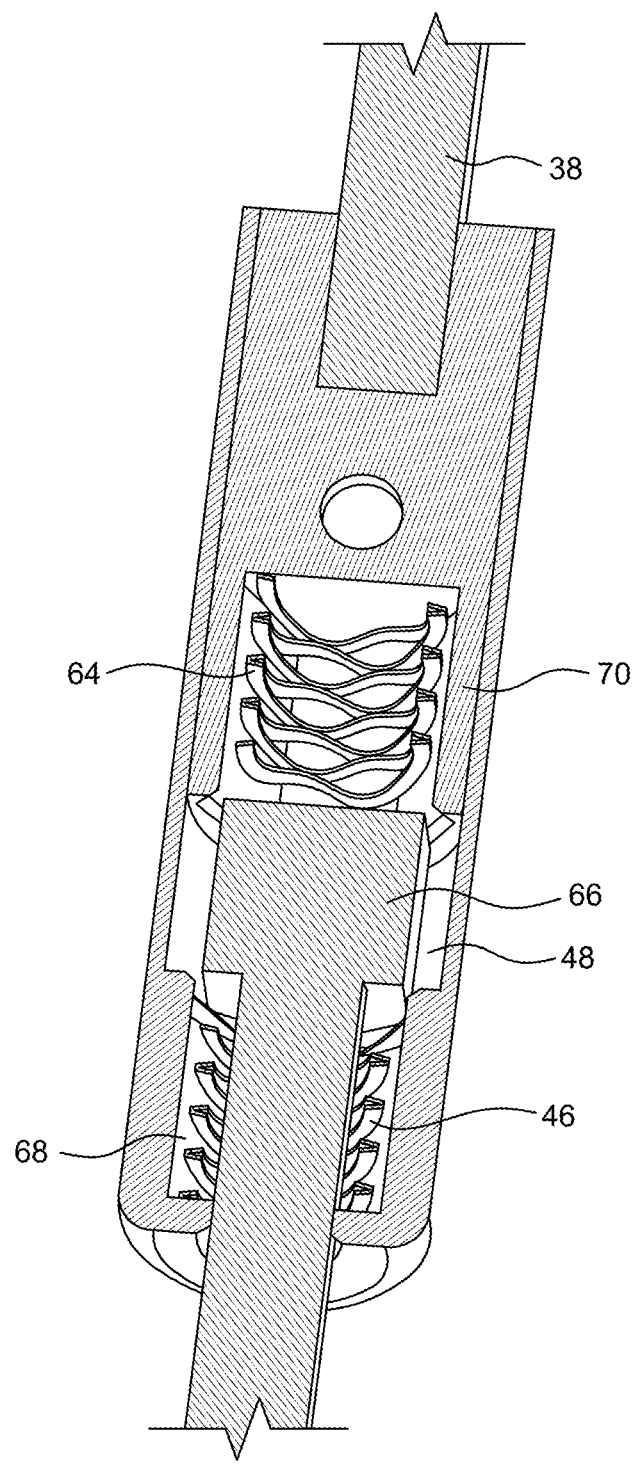
FIG. 22B is a detail view of the embodiment of FIG. 22A.

In another embodiment, as shown in FIGS. 22A and 22B, the surgical tool 12 may include a drill bit 32 and a drive shaft 38 that are configured to rotate about the horizontal axis in both a clockwise and a counter-clockwise direction. In this embodiment, the engagement system 30 further includes a second compression spring 64 and a hexagonal engagement system to facilitate rotation of the drill bit 32 in the counterclockwise direction. It should be understood that while this embodiment utilizes a hexagonal geometry, other shapes, such as star, hexalobe, square, etc., or a friction surface may be used.

When the user cuts through a first material 34, such as bone, the friction between the hole created and the shaft of the drill bit 32 can be difficult to overcome with only a static backwards force applied manually or mechanically. Rotating the dill bit in the opposite direction reduces the friction to make it easier to remove the drill bit 32 from the drilled hole. In this embodiment, when the tension required to compress the first compression spring 46 is overcome with forwards pressure, the male engagement hex 66 moves in to a female engagement pocket 68 disposed toward the distal end of the system, thereby engaging the drill bit in the clockwise direction. However, when the tension required to compress the second compression spring 64 is met with backwards pressure, the male engagement hex 66 engages the female engagement pocket 70 disposed toward the proximal end of the outer housing in order to allow the drill bit 32 to rotate in a counter-clockwise direction.

With certain details and embodiments of the present invention for systems and methods for robot-guided spinal decompression disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the claims that will ultimately be employed to protect this invention will define the scope of protection to be afforded to the patent holder. Those claims shall be deemed to include equivalent constructions insofar as they do not depart from the spirit and scope of the invention. Certain claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

What is claimed is:

1. A surgical tool for use in a system for removing bone from vertebrae to relieve stenosis, the surgical tool comprising:
   a drill bit having a proximal end and a distal end,
   a drive shaft having a proximal rod portion and a distal tubular portion, the drill bit and the drive shaft configured to rotate about a horizontal axis in a clockwise direction; and
   an engagement system disposed between the drill bit and the drive shaft; wherein the engagement system is configured to selectively engage the drill bit to the drive shaft for powered rotation when the drill bit contacts a first material at a first predetermined resistance and to disengage the drill bit from the drive shaft when the drill bit engages a second material at a second predetermined resistance; and wherein the first predetermined resistance is greater than the second predetermined resistance;
   wherein the engagement system comprises an outer housing, an inner housing, a base portion, and a first pressure sensing device; and
   wherein the distal tubular portion of the drive shaft comprises a contoured formation, the inner housing further comprises a contoured aperture, and the base portion comprises a pin that is disposed through the contoured aperture on the inner housing.

2. The surgical tool of claim 1, wherein the first pressure sensing device is disposed within the inner housing and positioned between the distal tubular portion of the drive shaft and the proximal end of the drill bit along the horizontal axis of the surgical tool.

3. The surgical tool of claim 2, wherein the pressure sensing device is a compression spring.

4. The surgical tool of claim 1, wherein the pressure sensing device is electronically activated.

5. The surgical tool of claim 4, wherein the pressure sensing device is a pressure gauge or a pressure sensing transducer.

6. The surgical tool of claim 1, wherein the pin is configured to move horizontally within the contoured aperture, and to fit within the contoured formation when the drill bit is exposed to the first predetermined resistance, and to move distally within the contoured aperture to disengage from the contoured formation when the drill bit is exposed to the second predetermined resistance.

7. The surgical tool of claim 1, wherein the surgical tool is configured to be controlled automatically by a robotic arm.

8. The surgical tool of claim 1, wherein the surgical tool is configured to be operated manually.

9. The surgical tool of claim 1, wherein the drill bit and the drive shaft are further configured to rotate about the horizontal axis in a counter-clockwise direction.

10. The surgical tool of claim 9, wherein the engagement system further comprises a second compression spring and an engagement hex configured to facilitate rotation of the drill bit in the counterclockwise direction.

11. A robot-guided spinal decompression system comprising:
- a surgical tool for use in a system for removing bone from vertebrae to relieve stenosis, the surgical tool comprising:
- a drill bit having a proximal end and a distal end,
- a drive shaft having a proximal rod portion and a distal tubular portion, the drill bit and the drive shaft configured to rotate about a horizontal axis in a clockwise direction; and
- an engagement system disposed between the drill bit and the drive shaft; wherein the engagement system is configured to selectively engage the drill bit to the drive shaft for powered rotation when the drill bit contacts a first material at a first predetermined resistance and to disengage the drill bit from the drive shaft when the drill bit engages a second material at a second predetermined resistance; and wherein the first predetermined resistance is greater than the second predetermined resistance;
- wherein the engagement system comprises an outer housing, an inner housing, a base portion, and a first compression spring; wherein the first compression spring is disposed within the inner housing and positioned between the distal tubular portion of the drive shaft and the proximal end of the drill bit along the horizontal axis of the surgical tool and the distal tubular portion of the drive shaft further comprises a contoured formation, the inner housing further comprises a contoured aperture, and the base portion comprises a pin that is disposed through the contoured aperture on the inner housing; and
- a robotic arm; wherein the surgical tool is configured to be controlled by the robotic arm and wherein the robotic arm has a range of motion to facilitate movement of the surgical tool in a predetermined pattern by operation of the robotic arm.

12. The system of claim 11, wherein the pin is configured to move horizontally within the contoured aperture, and to fit within the contoured formation when the drill bit is exposed to the first predetermined resistance, and to move distally within the contoured aperture to disengage from the contoured formation when the drill bit is exposed to the second predetermined resistance.

13. The system of claim 11, wherein the drill bit and the drive shaft are further configured to rotate about the horizontal axis in a counter-clockwise direction.

14. The system of claim 13, wherein the engagement system further comprises a second compression spring and an engagement hex configured to facilitate rotation of the drill bit in the counterclockwise direction.

15. The system of claim 11, wherein the predetermined pattern is derived from pre-surgery computer scanning and planning.

16. The system of claim 11, wherein the system further comprises an image acquisition device operably associated with the robotic arm to facilitate acquisition of images of an area of operation.

17. The system of claim 11, wherein the system further comprises a computer operable to control movement of the robotic arm and operation of the surgical tool.

* * * * *